United States Patent [19]
Smith et al.

[11] Patent Number: 5,171,534
[45] Date of Patent: Dec. 15, 1992

[54] AUTOMATED DNA SEQUENCING TECHNIQUE

[75] Inventors: Lloyd M. Smith, Madison, Wis.; Leroy E. Hood, Pasadena, Calif.; Michael W. Hunkapiller, San Carlos, Calif.; Tim J. Hunkapiller, Pasadena, Calif.

[73] Assignee: California Institute of Technology, Pasadena, Calif.

[21] Appl. No.: 558,312

[22] Filed: Oct. 15, 1990

Related U.S. Application Data

[60] Division of Ser. No. 106,232, Oct. 7, 1987, abandoned, which is a continuation-in-part of Ser. No. 722,742, Apr. 11, 1985, abandoned, which is a continuation-in-part of Ser. No. 689,013, Jan. 2, 1985, abandoned, which is a continuation-in-part of Ser. No. 570,973, Jan. 16, 1984, abandoned.

[51] Int. Cl.⁵ .................. C07K 3/14; G01N 33/561
[52] U.S. Cl. .................. 422/82.05; 204/182.8; 204/299 R; 422/116; 435/6; 436/94; 935/78
[58] Field of Search ............ 422/116, 82.05; 435/6; 436/94; 935/77-78, 85-87; 204/299 R, 182.8

[56] References Cited

U.S. PATENT DOCUMENTS

| | | | |
|---|---|---|---|
| 4,119,521 | 10/1978 | Chirikjian | 204/299 R |
| 4,151,065 | 4/1979 | Kaplan et al. | 935/19 |
| 4,318,846 | 3/1982 | Khanna et al. | 424/88 |
| 4,534,647 | 8/1985 | Gross et al. | 204/299 R |
| 4,855,225 | 8/1989 | Fung et al. | 536/26 |

FOREIGN PATENT DOCUMENTS 0044648  9/1982  Japan ............ 204/299 R

*Primary Examiner*—Jill A. Johnston
*Attorney, Agent, or Firm*—Joseph E. Mueth

[57] ABSTRACT

A system for the electrophoretic analysis of DNA fragments produced in DNA sequencing operations comprising: a source of chromophore or fluorescent tagged DNA fragments; a zone for contacting an electrophoresis gel; means for introducing said tagged DNA fragments to said zone; and photometric means for monitoring said tagged DNA fragments as they move through said gel.

7 Claims, 6 Drawing Sheets

FIG. 1A.

5'...ATGCTCTGCAGGAATAC...3'    5'...ATGCTCTGCA 3'      5' GGAATAC...3'
3'...TACGAGACGTCCTTATG...5'  →  3'...TACGAG     5'  +  3' ACGTCCTTATG...5'
              PST I

FIG. 1B.

5'...ATGCTCTGCA 3'      5' ACGTNNT—FITC 3'         5'...ATGCTCTGCA      3'
3'...TACGAG    5'   +   3' NNTGCA       5'   →    3'...TACGAGACGTNNT—FITC
                                              T4 DNA

FIG. 3(I).    A HYPOTHETICAL DNA SEQUENCE
5' ACGTGCTACTGA 3'

FIG. 3(II).   IDEALIZED AUTORADIOGRAM OF POLYACRYLAMIDE
SLAB GEL PRODUCED IN CHAIN TERMINATION
SEQUENCING ACCORDING TO THE PRIOR ART

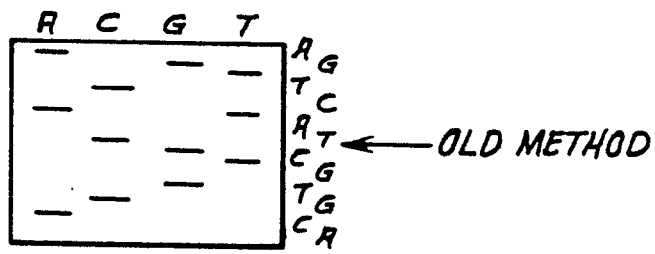

FIG. 3(III).  IDEALIZED DIAGRAM OF COLORED DNA
BANDS ON TUBE ACRYLAMIDE GEL, PRODUCED
ACCORDING TO PRESENT INVENTION

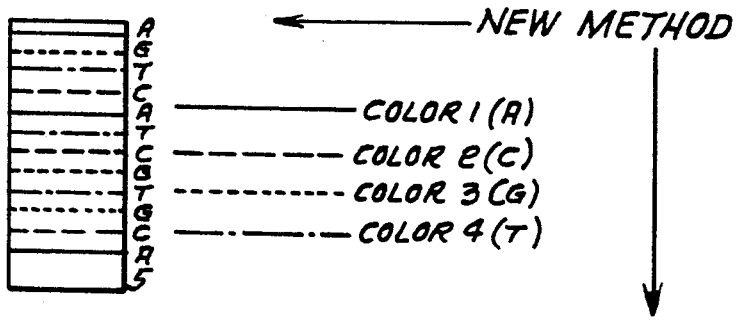

FIG. 3(IV).   IDEALIZED OUTPUT FROM DETECTION OF
COLORED BANDS ON ABOVE TUBE GEL

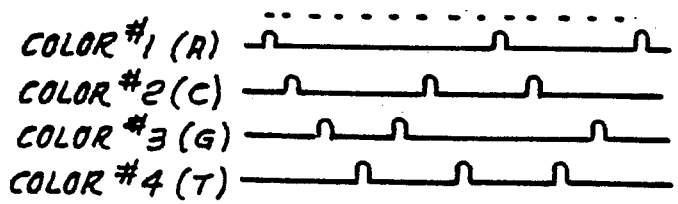

AUTOMATED DNA SEQUENCING TECHNIQUE

CROSS REFERENCE TO RELATED APPLICATIONS

This application is a divisional of Ser. No. 106,232, filed Oct. 7, 1987, abandoned, which in turn was a continuation-in-part of U.S. Ser. No. 722,742, filed Apr. 11, 1985 (now abandoned) which was a continuation-in-part of U.S. Ser. No. 689,013 filed Jan. 2, 1985 (now abandoned) which, in turn, was a continuation-in-part of U.S. Ser. No. 570,973 filed Jan. 16, 1984, now abandoned.

BACKGROUND OF THE INVENTION

The development of reliable methods for sequence analysis of DNA (deoxyribonucleic acid) and RNA (ribonucleic acid) has been one of the keys to the success of recombinant DNA and genetic engineering. When used with the other techniques of modern molecular biology, nucleic acid sequencing allows dissection and analysis of animal, plant and viral genomes into discrete genes with defined chemical structure. Since the function of a biological molecule is determined by its structure, defining the structure of a gene is crucial to the eventual manipulation of this basic unit of hereditary information in useful ways. Once genes can be isolated and characterized, they can be modified to produce desired changes in their structure that allow the production of gene products—proteins—with different properties than those possessed by the original proteins. Microorganisms into which the natural or synthetic genes are placed can be used as chemical "factories" to produce large amounts of scarce human proteins such as interferon, growth hormone, and insulin. Plants can be given the genetic information to allow them to survive harsh environmental conditions or produce their own fertilizer.

The development of modern nucleic acid sequencing methods involved parallel developments in a variety of techniques. One was the emergence of simple and reliable methods for cloning small to medium-sized strands of DNA into bacterial plasmids, bacteriophages, and small animal viruses. This allowed the production of pure DNA in sufficient quantities to allow its chemical analysis. Another was the near perfection of gel electrophoretic methods for high resolution separation of oligonucleotides on the basis of their size. The key conceptual development, however, was the introduction of methods of generating size-nested sets of fragments cloned, purified DNA that contain, in their collection of lengths, the information necessary to define the sequence of the nucleotides comprising the parent DNA molecules.

Two DNA sequencing methods are in widespread use. These are the method of Sanger, F., Nicken, S. and Coulson, A. R. Proc. Natl. Acad. Sci. USA 74, 5463 (1977) and the method of Maxam, A. M. and Gilbert, W. Methods in Enzymology 65, 499–599 (1980).

The method developed by Sanger is referred to as the dideoxy chain termination method. In the most commonly used variation of this method, a DNA segment is cloned into a single-stranded DNA phage such as M13. These phage DNAs can serve as templates for the primed synthesis of the complementary strand by the Klenow fragment of DNA polymerase I. The primer is either a synthetic oligonucleotide or a restriction fragment isolated from the parental recombinant DNA that hybridizes specifically to a region of the M13 vector near the 3" end of the cloned insert. In each of four sequencing reactions, the primed synthesis is carried out in the presence of enough of the dideoxy analog of one of the four possible deoxynucleotides so that the growing chains are randomly terminated by the incorporation of these "deadend" nucleotides. The relative concentration of dideoxy to deoxy forms is adjusted to give a spread of termination events corresponding to all the possible chain lengths that can be resolved by gel electrophoresis. The products from each of the four primed synthesis reactions are then separated on individuals tracks of polyacrylamide gels by the electrophoresis. Radioactive tags incorporated in the growing chains are used to develop an autoradiogram image of the pattern of the DNA in each electrophoresis track. The sequence of the deoxynucleotides in the cloned DNA is determined from an examination of the pattern of bands in the four lanes.

The method developed by Maxam and Gilbert uses chemical treatment of purified DNA to generate size-nested sets of DNA fragments analogous to those produced by the Sanger method. Single or double-stranded DNA, labeled with radioactive phosphate at either the 3' or 5' end, can be sequenced by this procedure. In four sets of reactions, cleavage is induced at one or two of the four nucleotide bases by chemical treatment. Cleavage involves a threestage process: modification of the base, removal of the modified base from its sugar, and strand scission at that sugar. Reaction conditions are adjusted so that the majority of end-labeled fragments generated are in the size range (typically 1 to 400 nucleotides) that can be resolved by gel electrophoresis. The electrophoresis, autoradiography, and pattern analysis are carried out essentially as is done for the Sanger method. (Although the chemical fragmentation necessarily generates two pieces of DNA each time it occurs, only the piece containing the end label is detected on the autoradiogram.)

Both of these DNA sequencing methods are in widespread use, and each has several variations.

For each, the length of sequence that can be obtained from a single set of reactions is limited primarily by the resolution of the polyacrylamide gels used for electrophoresis. Typically, 200 to 400 bases can be read from a single set of gel tracks. Although successful, both methods have serious drawbacks, problems associated primarily with the electrophoresis procedure. One problem is the requirement of the use of radiolabel as a tag for the location of the DNA bands in the gels. One has to contend with the short half-life of phosphorus-32, and hence the instability of the radiolabeling reagents, and with the problems of radioactive disposal and handling. More importantly, the nature of autoradiography (the film image of a radioactive gel band is broader than the band itself) and the comparison of band positions between four different gel tracks (which may or may not behave uniformly in terms of band mobilities) can limit the observed resolution of bands and hence the length of sequence that can be read from the gels. In addition, the track-to-track irregularities make automated scanning of the autoradiograms difficult—the human eye can presently compensate for these irregularities much better than computers can. This need for manual "reading" of the autoradiograms is time-consuming, tedious and error-prone. Moreover, one cannot read the gel patterns while the electrophoresis is actually being performed, so as to be able to terminate the electrophoresis once resolution becomes insufficient to separate adjoining bands, but must terminate the electrophoresis at some standardized time and wait for the autoradiogram to be developed before the sequence reading can begin.

The invention of the present patent application addresses these and other problems associated with DNA sequencing procedures and is believed to represent a significant advance in the art. The preferred embodiment of the present invention represents a further and distinct improvement.

SUMMARY OF THE INVENTION

Briefly, this invention comprises a novel process for the electrophoretic analysis of DNA fragments produced in DNA sequencing operations wherein chromophores or fluorophores are used to tag the DNA fragments produced by the sequencing chemistry and permit the detection and characterization of the fragments as they are resolved by electrophoresis through a gel. The detection employs an absorption or fluorescent photometer capable of monitoring the tagged bands as they are moving through the gel.

This invention further comprises a novel process for the electrophoretic analysis of DNA fragments produced in DNA sequencing operations wherein a set of four chromophores are used to tag the DNA fragments produced by the sequencing chemistry and permit the detection and characterization of the fragments as they are resolved by electrophoresis through a gel; the improvement wherein the four different fragment sets are tagged with the fluorophores fluorescein, Texas Red, tetramethyl rhodamine, and 7-nitro-benzofurazan.

This invention also includes a novel system for the electrophoretic analysis of DNA fragments produced in DNA sequencing operations comprising:

a source of chromophore or fluorescent tagged DNA fragments.

a zone for containing an electrophoresis gel, means for introducing said tagged DNA fragments to said zone; and photometric means for monitoring or detecting said tagged DNA fragments as they move through and are separated by said gel.

It is an object of this invention to provide a novel process for the sequence analysis of DNA.

It is another object of our invention to provide a novel system for the analysis of DNA fragments.

More particularly, it is an object of this invention to provide an improved process for the sequence analysis of DNA.

These and other objects and advantages of this invention will be apparent from the detailed description which follows.

DETAILED DESCRIPTION OF THE INVENTION

Turning to the drawings:

FIG. 1 is an illustration of one means of end-labeling a DNA fragment with a fluorescent tag. Pst. I and T4 DNA ligase are enzymes commonly used in recombinant DNA research.

FIG. 1A pertains to PST I DNA ligase. FIG. 1B pertains to T4 DNA ligase.

FIG. 3 is a comparison of the type of data produced by DNA sequencing of the sequence shown in FIG. 1.

FIG. 3I shows a hypothetical DNA sequence.

FIG. 3II shows an idealized autoradiogram of polyacrylamide slab gel produced by the chain termination method according to the prior art.

FIG. 3III shows an idealized diagram of DNA on an acrylamide gel, produced according to the present invention.

FIG. 3IV shows an idealized output from the detection on colored bands on the acrylamide gel of FIG. 3III.

Figure 4:
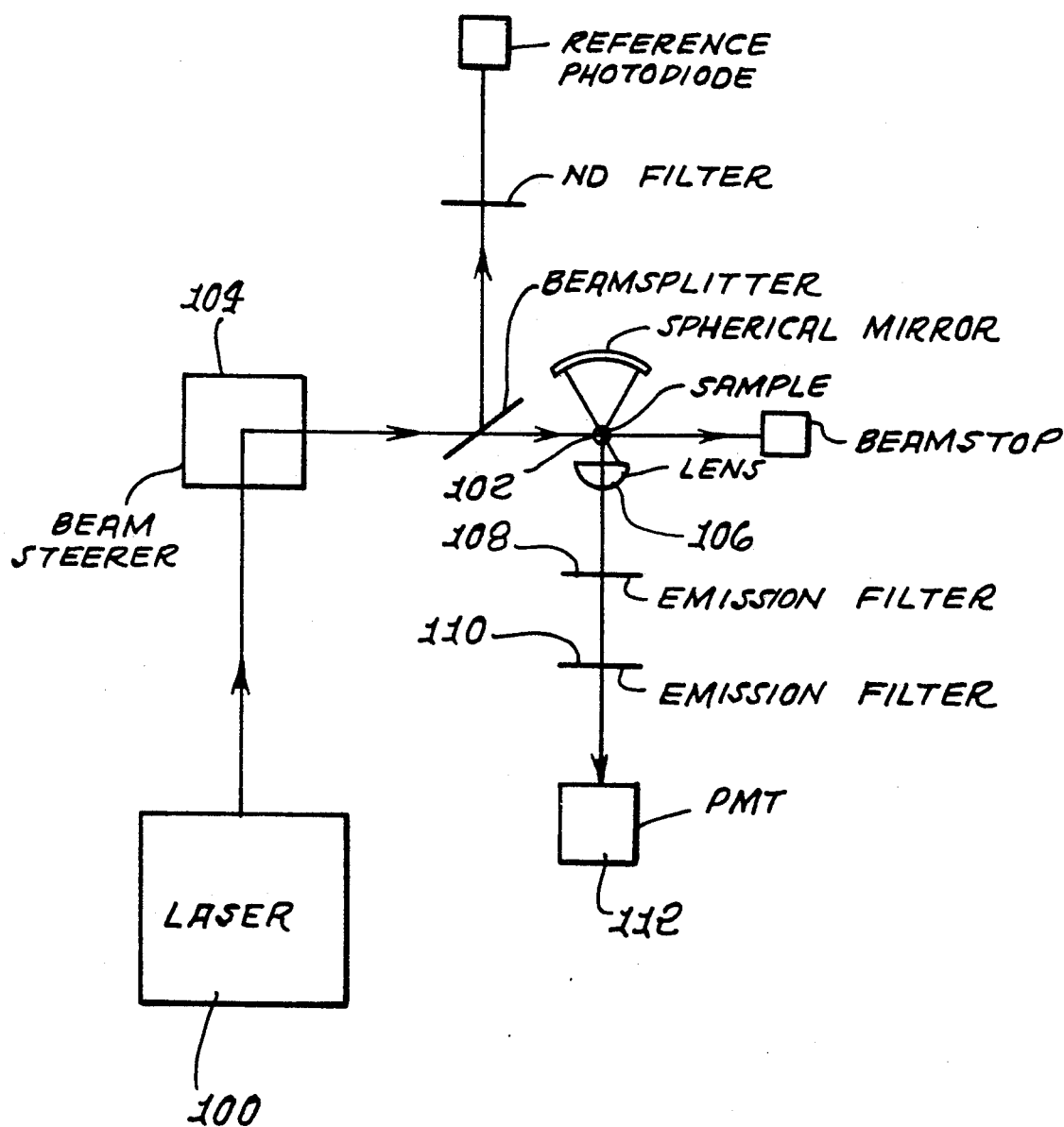

FIG. 4 is a block diagram of a preferred DNA sequencer according to this invention.

Figure 5:
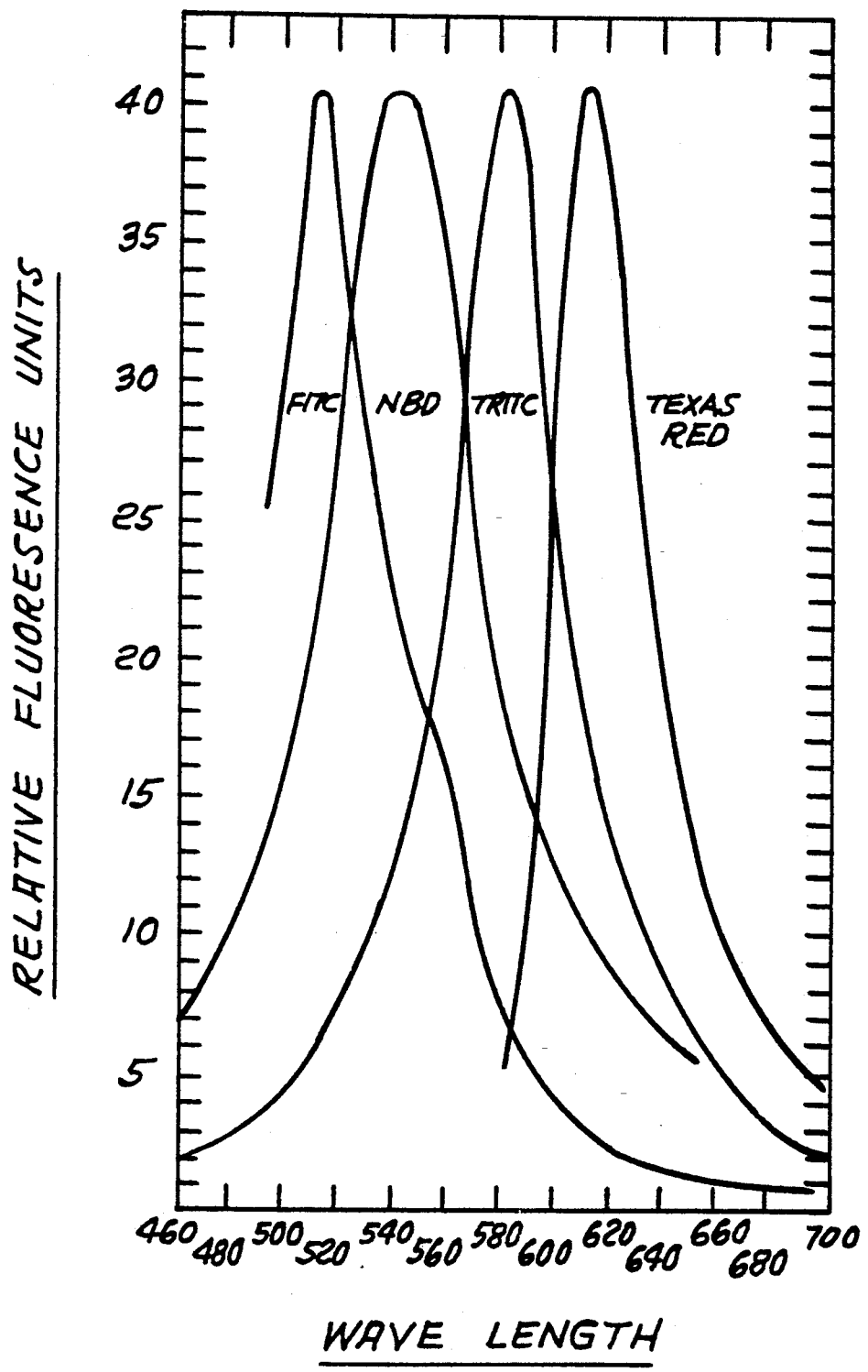

FIG. 5 shows the emission spectra for the four fluorophores used as tags in the preferred embodiment of this invention.

Figure 6:
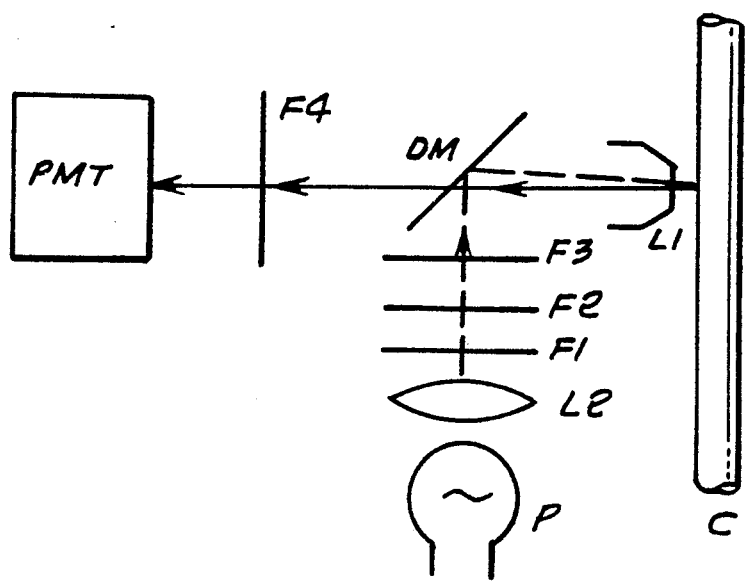

FIG. 6 is a schematic diagram of a possible optical configuration in the detector unit. P, lamp source; L1, objective lens; L2, collimating lens; F1, UV blocking filter; F2, heat blocking filter; F3, band pass excitation filter; F4, long pass emission filter; DM, dichroic mirror; C, polyacrylamide gel; PMT, photomultiplier tube.

Figure 7:
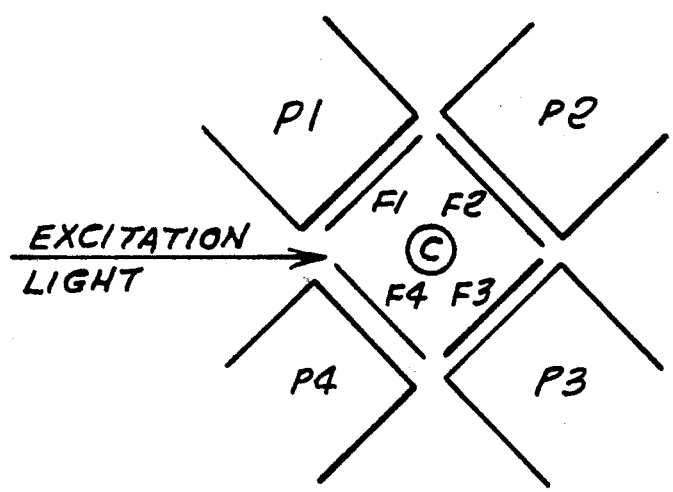

FIG. 7 is a schematic diagram of another possible optical configuration in the detector unit. F1 to F4 are bandpass filters centered at the emission maximum of the different dyes. P1 to P4 are photomultiplier tubes. The excitation light is of a wavelength such that it is not transmitted through any of the filters F1 to F4.

In the previous methods of DNA sequencing, including those based on the Sanger dideoxy chain termination method, a single radioactive label, phosphorus-32, is used to identify all bands on the gels. This necessitates that the fragment sets produced in the four synthesis reactions be run on separate gel tracks and leads to the problems associated with comparing band mobilities in the different tracks. This problem is overcome in the present invention by the use of a set of four chromophores or fluorophores with different absorption or fluorescent maxima, respectively. Each of these tags is coupled chemically to the primer used to initiate the synthesis of the fragment strands. In turn, each tagged primer is then paired with one of the dideoxynucleotides and used in the primed synthesis reaction with the Klenow fragment of DNA polymerase.

The primers must have the following characteristics. 1) They must have a free 3'hydroxyl group to allow chain extension by the polymerase. 2) They must be complementary to a unique region 3' of the cloned insert. 3) They must be sufficiently long to hybridize to form a unique, stable duplex. 4) The chromophore or fluorophore must not interfere with the hybridization or prevent 3'-end extension by the polymerase.

Conditions 1, 2 and 3 above are satisfied by several synthetic oligonucleotide primers which are in general use for Sanger-type sequencing utilizing M13 vectors.

One such primer is the 15 mer 5' CCC AG TCA CGA CGT T 3' where A, C, G and T represent the four different nucleoside components of DNA; A, adenosine; C, cytosine; G, guanosine; T, thymidine.

In the preferred embodiment of the present invention a set of four fluorophores with different emission spectra, respectively, are used. These different emission spectra are shown in FIG. 5. Each of these tags is coupled chemically to the primer used to initiate the synthesis of the fragment strands. In turn, each tagged primer is then paired with one of the dideoxynucleotides and used in the primed synthesis reaction with the Klenow fragment of DNA polymerase.

The dyes used must have high extinction coefficients and/or reasonably high quantum yields for fluorescence. They must have well resolved adsorption maxima and/or emission masima. Representative of such amino reactive dues are: fluorescein isothiocyanage (FITC, $\lambda_{max}{}^{Ex}=495$, $\lambda_{max}{}^{Em}=520$, $\epsilon_{495}\simeq 8\times 10^4$), tetramethyl rhodamine isothiocyanate (TMRITC, $\lambda_{max}{}^{Ex}=550$, $\lambda_{max}{}^{Em}=578$, $\epsilon_{550}\simeq 4\times 10^4$), and substituted rhodamine isothiocyanate (XRITC, $\lambda=580$, $\lambda_{max}{}^{Em}=604$, $\epsilon_{580}\simeq 8\times 10^4$) where $\lambda$ represents the wavelength in nanometers, Ex is excitation, Em is emission, max is maximum, and $\epsilon$ is the molar extinction coefficient. These dyes have been attached to the M13 primer and the conjugates electrophoresed on a 20% polyacrylamide gel. The labeled primers are visible by both their absorption and their fluorescence in the gel. All four labeled primers have identical electrophoretic mobilities. The dye conjugated primers retain their ability to specifically hybridize to DNA, as demonstrated by their ability to replace the underivitized oligonucleotide normally used in the sequencing reactions.

The chemistry for the coupling of the chromophoric or fluorophoric tags is described in assignee's copending patent applications Ser. No. 565,010, filed Dec. 20, 1983, now abandoned, and Ser. No. 709,579, filed Mar. 8, 1985, (now abandoned), and Ser. No. 878,045 filed Jun. 24, 1985, and now issued as U.S. Pat. No. 4,849,513 the disclosures of which are expressly incorporated herein by reference. The strategy used is to introduce an aliphatic amino group at the 5' terminus as the last addition in the synthesis of the oligonucleotide primer. This reactive amino group may then readily be coupled with a wide variety of amino reactive fluorophores or chromophores. This approach aids compatibility of the labeled primers with condition 4 above.

End labeling of DNA for use with Maxam/Gilbert method. In the Maxam/Gilbert method of DNA sequencing, the end of the piece of DNA whose sequence is to be determined must be labeled. This is conventionally done enzymatically using radioactive nucleosides. In order to use the Maxam/Gilbert method in conjunction with the dye detection scheme described in this invention, the DNA piece must be labeled with dyes. One manner in which this may be accomplished is shown in FIG. 1. Certain restriction endonucleases generate what is known as a 3' overhang as the product of DNA cleavage. These enzymes generate a "sticky end," a short stretch of single stranded DNA at the end of a piece of double stranded DNA. This region will anneal with a complementary stretch of DNA, which may be covalently joined to the duplex DNA with the enzyme ligase. In this manner one of the strands is covalently linked to a detectable moiety. This moiety may be a dye, an amino group or a protected amino group (which could be deprotected and reacted with dye subsequent to the chemical reactions).

Sequencing reactions. The dideoxy sequencing reactions are performed in the standard fashion Smith, A. J. H., Methods in Enzymology 65, 56-580 (1980), except that the scale may be increased if necessary to provide an adequate signal intensity in each band for detection. The reactions are done using a different color primer for each different reaction. No radiolabeled nucleoside triphosphate need be included in the sequencing reaction.

The Maxam/Gilbert sequencing reactions are performed in the usual manner, Gil, S.F.Aldrichimica Acta 16(3), 59-61 (1983), except that the end label is either one or four colored dyes, or a free or protected amino group which may be reacted with dye subsequently.

Detection. There are many different ways in which the tagged molecules which have been separated by length using polyacrylamide gel electrophoresis may be detected. Four illustrative modes are described below. These are i) detection of the fluorescence excited by light of different wavelengths for the different dyes, ii) detection of fluorescence excited by light of the same wavelength for the different dyes, iii) elution of the molecules from the gel and detection by chemiluminescence, and iv) detection by the absorption of light by molecules. In modes i) and ii) the fluorescence detector should fulfill the following requirements. a) The excitation light beam should not have a height substantially greater than the height of a band. This is normally in the range of 0.1 to 0.5 mm. The use of such a narrow excitation beam allows the attainment of maximum resolution of bands. b) The excitation wavelength can be varied to match the absorption maxima of each of the different dyes or can be a single narrow, high intensity light band that excites all four fluorophores and does not overlap with any of the fluorescence emission. c) The optical configuration should minimize the flux of scattered and reflected excitation light to the photodetector 14. The optical filters to block out scattered and reflected excitation light are varied as the excitation wavelength is varied. d) The photodetector 14 should have a fairly low noise level and a good spectral response and quantum efficiency throughout the range of the emission of the dyes (500 to 600 nm for the dyes listed above). e) The optical system for collection of the emitted fluorescence should have a high numerical aperture. This maximizes the fluorescence signal. Furthermore, the depth of field of the collection optics should include the entire width of the column matrix.

Two illustrative fluorescence detection systems are diagrammed in FIGS. 6 and 7. The system in FIG. 6 is compatible with either single wavelength excitation or multi wavelength excitation. For single wavelength excitation, the filter F4 is one of four band pass filters centered at the peak emission wavelength of each of the dyes. This filter is switched every few seconds to allow continual monitoring of each of the four fluorophores. For multi wavelength excitation, the optical elements F3 (excitation filter), DM (dichroic mirror), and F4 (barrier filter) are switched together. In this manner both the excitation light and the observed emission light are varied. The system in FIG. 7 is a good arrangement for the case of single wavelength excitation. This system has the advantage that no moving parts are required, and fluorescence from all four of the dyes may be simultaneously and continuously monitored. A third approach (iii above) to detection is to elute the labeled molecules at the bottom of the gel, combine them with an agent for excitation of chemiluminescence such as 1,2 dioxetane dione, Gill, S.K. Aldrichimica Acta 16(3), 59-61 (1983); Mellbin, G. J. Liq. Chrom. 6(9), 1603-1616 (1983), and flow the mixture directly into a detector which can measure the emitted light at four separate wavelengths. The background signal in chemiluminescence is much lower than in fluorescence, resulting in higher signal to noise ratios and increased sensitivity. Finally, the measurement may be made by measurements of light absorption (iv above). In this case, a light beam of variable wavelength is passed through the gel, and the decrease in the beam intensity due to absorption of light at the different wavelengths corresponding to the absorption maximum of the four dyes, it is possible to determine which dye molecule is in the light path. As disadvantage of this type of measurement is that absorption measurements are inherently less sensitive than fluorescence measurements.

The above-described detection system is interfaced to a computer 16. In each time interval examined, the computer 16 receives a signal proportional to the measured signal intensity at that time for each of the four colored tags. This information tells which nucleotide terminates the DNA fragment of the particular length in the observation window at that time. The temporal sequence of colored bands gives the DNA sequence. In FIG. 3 is shown the type of data obtained by conventional methods, as well as the type of data obtained by the improvements described in this invention.

The following Examples are presented solely to illustrate the invention. In the Examples, parts and percentages are by weight unless otherwise indicated.

EXAMPLE I

Figure 2:
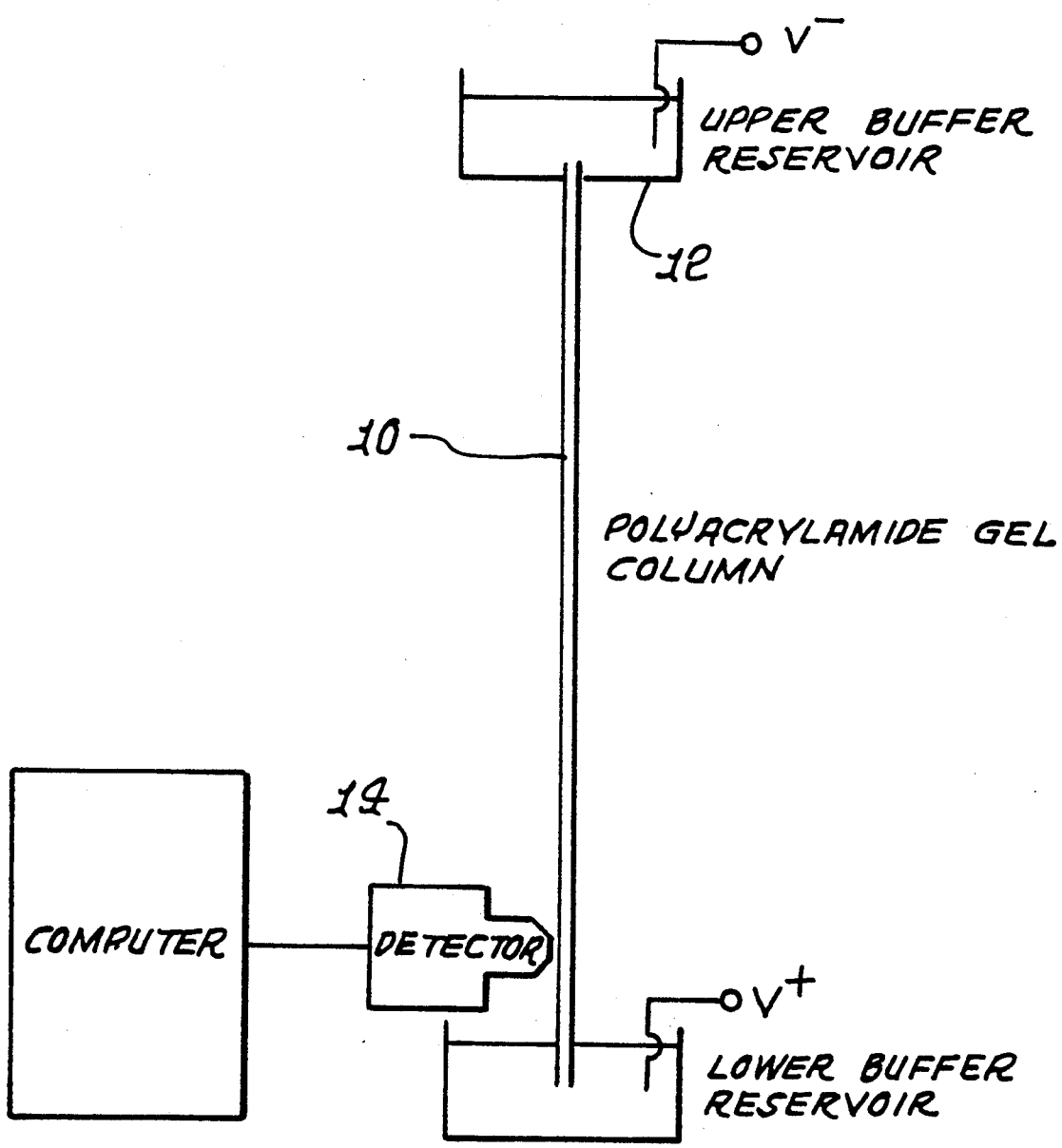
FIG. 2 is a block diagram of automated DNA sequencer, gel electrophoretic system.

Gel electrophoresis. Aliquots of the sequencing reactions are combined and loaded onto a 5% polyacrylamide column 10 shown in FIG. 2 from the upper reservoir 12. The relative amounts of the four different reactions in the mixture are empirically adjusted to give approximately the same fluorescence or absorptive signal intensity from each of the dye DNA conjugates. This permits compensation for differences in dye extinction coefficients, dye fluorescence quantum yields, detector sensitivities and so on. A high voltage is placed across the column 10 so as to electrophorese the labeled DNA fragments through the gel. The labeled DNA segments differing in length by a single nucleotide are separated by electrophoresis in this gel matrix. At or near the bottom of the gel column 10, the bands of DNA are resolved from one another and pass through the detector 14 (more fully described above). The detector 14 detects the fluorescent or chromophoric bands of DNA in the gel and determines their color, and therefore to which nucleotide they correspond. This information yields the DNA sequence.

EXAMPLE II

FIG. 4 shows a block diagram of a DNA sequenator for use with one dye at a time. The beam (4880 A) from an argon ion laser 100 is passed into the polyacrylamide gel tube (sample) 102 by means of a beamsteerer 104. Fluorescence exited by the beam is collected using a low f-number lens 106, passed through an appropriate set of optical filters 108 and 110 to eliminate scattered excitation light and detected using a photomultiplier tube (PMT) 112. The signal is readily detected on a strip chart recorder. DNA sequencing reactions are carried out utlizing a fluorescein labeled oligonucletide primer. The peaks on the chart correspond to fragments to fluorescein labeled DNA of varying lengths synthesized in the sequencing reactions and separated in the gel tube by electrophoresis. Each peak contains on the order of $10^{-15}$ to $10^{-16}$ moles of fluorescein, which is approximately equal to the amount of DNA obtained per band in an equivalent sequencing gel utilizing radioisotope detection. This proves that the fluorescent tag is not removed or degraded from the oligonucleotide primer in the sequencing reactions. It also demonstrates that the detection sensitivity is quite adequate to perform DNA sequence analysis by this means.

MATERIALS

Fluorescein-5-isothiocyanate (FITC) and Texas Red were obtained from Molecular Probes, Inc. (Junction City, Oreg.). Tetramethyl rhodamine isothiocyanate (TMRITC) was obtained from Research Organics, Inc. (Cleveland, Ohio). 4-fluoro-7-nitro-benzofurazan (NBD-fluoride) was obtained from Sigma Chemical Co. (St. Louis, Mo.). Absorption spectra were obtained on a H/P 8491 spectrophotometer. High performance liquid chromatography was performed on a system composed of two Altex 110A pumps, a dual chamber gradient mixer, Rheodyne injector, Kratos 757 UV detector, and an Axxiom 710 controller.

EXAMPLE III

Addition of 5'-aminothymidine phosphoramidites to oligonuleotides

The protected 5'-aminothymidine phosphoramidites, 5'-(N-9-fluorenylmethyloxycarbonyl)-5'-amino-5'-deoxy-3'-N,N-diisopropylaminomethoxyphosphinyl thymidine, is coupled to the 5'-hydroxyl of an oligonucleotide using well established DNA synthetic procedures. The solvents and reaction conditions used are identical to those used in oligonucleotide synthesis.

EXAMPLE IV

Dye conjugation

The basic procedure used for the attachment of fluorescent dye molecules to the amino oligonucleotides is to combine the amino oligonucleotide and the dye in aqueous solution buffered to pH 9, to allow the reaction to stand at room temperature for several hours, and then to purify the product in two stages. The first purification step is to remove the bulk of the unreacted or hydrolyzed dye by gel filtration. The second purification stage is to separate the dye conjugate from unreacted oligonucleotide by reverse phase high performance liquid chromatography. Slight variations upon these conditions are employed for the different dyes, and the specific procedures and conditions used for four particular dyes are given below and in Table 1.

TABLE 1

| Reverse Phase HPLC Conditions for Dye-oligonucleotide Purification | |
|---|---|
| Sample | Retention time |
| PLP-15[a] | 18' |
| PLP-15-T-NH$_2$[b] | 18' |
| FITC PLP-15[c] | 27' |
| NBD PLP-15 | 25' |
| TMRITC PLP-15 | 32' and 34'[d] |
| Texas Red PLP-15 | 42' |

[a]PLP-15 is an oligonucleotide primer for DNA sequence analysis in the M13 vectors. Its sequence is 5'CCC AGT CAC GAC FTT 3'.
[b]PLP-15-T-NH$_2$ is the oligonucleotide PLP-15 to which a 5'-amino-5'-deoxythymidine base has been added to==at the 5' terminus.
[c]The nomenclature Dye PLP-15 signifies the conjugate of PLP-15-T-NH$_2$ and the dye molecule.
[d]Two fluorescent oligonucleotide products were obtained with TMRITC. Both were equally effective in sequencing. This is presumed to be due to the two isomers of TMRITC which are present in the commercially available material.

Retention times shown are for HPLC gradients of 20% solvent B/80% solvent A to 60% solvent B/40% solvent A in 40 min., where solvent A is 0.1M triethylammonium acetate pH 7.0 and solvent B is 50% acetonitrile, 50% 0.1M triethylammonium acetate pH 7.0. The column was an Axxiom ODS 5 micron C 18 column #555-102 available from Cole Scientific, Calabasas, Calif. This gradient is not optimized for purification of PLP-15 and PLP-15-T-NH$_2$, but the retention times are included for comparison with the dye primer conjugates.

The following procedure is for use with fluorescein isothiocyanate or 4-fluoro-7-nitro-benzofurazan. Amino oligonucleotide (0.1 ml of ~1 mg/ml oligonucleotide in water) is combined with 1M sodium carbonate/bicarbonate buffer pH 9 (50 μl), 10 mg/ml dye in dimethylformamide (20 μl) and H$_2$O (80 μl). This mixture is kept in the dark at room temperature for several hours. The mixture is applied to a 10 ml column of Sephadex G-25 (medium) and the colored band of material eluting in the excluded volume is collected. The column is equilibrated and run in water. In control reactions with underivatized oligonucleotides, very little if any dye is associated with the oligonucleotide eluting in the void volume. The colored material is further purified by reverse phase high performance liquid chromatography on an Axxiom C$_{18}$ column (#555-102, Cole Scientific, Calabasas, Calif.) in a linear gradient of acetonitrile:0.1M triethylammonium acetate, pH 7.0. It is convenient for this separation to run the column eluant through both a UV detector (for detecting the DNA absorbance) and a fluorescence detector (for detecting the dye moiety). The desired product is a peak on the chromatogram which is both strongly UV absorbing and strongly fluorescent. The dye oligonucleotide conjugates elute at higher acetonitrile concentrations than the oligonucleotides alone, as shown in Table 1. The oligonucleotide is obtained from the high performance liquid chromatographyin solution in a mixture of acetonitrile and 0.1M triethylammonium acetate buffer. This is removed by lyophilization and the resulting material is redissolved by vortexing in 10 mM sodium hydroxide (for a minimum amount of time) followed by neutralization with a five fold molar excess (to sodium hydroxide) of Tris buffer, pH 7.5.

The conjugation with Texas Red is identical to that described for fluorescein isothiocyanate and 4-fluoro-7-nitro-benzofurazan, except that:

a) prior to separation on Sephadex G-25 the reaction is made 1M in ammonium acetate and kept at room temperature for 30 minutes, and b) the Sephadex G-25 column is run in 0.1M ammonium acetate. This largely eliminates nonspecific binding of the dye molecule to the oligonucleotide.

The conjugation with tetramethyl rhodamine isothiocyanate is identical to that for Texas Red except that the reaction is carried out in 10 mM sodium carbonate/bicarbonate buffer, pH 9.0, and 50% dioxane. This increases solubility of the tetramethyl rhodamine and a much higher yield of dye oligonucleotide conjugate is obtained.

In some cases, particularly with the rhodamine-like dyes, a substantial amount of nonspecific binding of dye was observed, as manifested by an inappropriately large dye absorption present in the material eluted from the gel filtration column. In these cases the material was concentrated and reapplied to a second gel filtration column prior to high performance liquid chromatography purification. This generally removed the majority of the noncovalently associated dye.

EXAMPLE V

Properties of dye-oligonucleotide conjugates

The development of chemistry for the synthesis of dye oligonucleotide conjugates allows their use as primers in DNA sequence analysis. Various fluorescent dye primers have been tested by substituting them for the normal primer in DNA sequence analysis by the enzymatic method. An autoradiogram of a DNA sequencing gel in which these dye-conjugated primers were utilized in T reactions in place of the normal oligonucleotide primer was prepared. This autoradiogram was obtained by conventional methods employing α-$^{32}$PdCTP as a radiolabel. The autoradiogram showed that the underivitized primer, amino-derivitized primer, and dye conjugated primers all give the same pattern of bands (corresponding to the DNA sequence), indicating that the derivitized primers retain their ability to hybridize specifically to the complementary strand. Secondly, the bands generated using the different primers differ in their mobilities, showing that it is indeed the dye-primers which are responsible for the observed pattern, and not a contaminant of unreacted or underivitized oligonucleotide. Thirdly, the intensity of the bands obtained with the different primers is comparable, indicating that the strength of hybridization is not significantly perturbed by the presence of the dye molecules.

The separations are again carried out in an acrylamide gel column. The beam from an argon ion laser is passed into the polyacrylamide gel tube (sample) by means of a beamsteerer. Fluorescence exited by the beam is collected using a low f-number lens, passed through an appropriate set of optical filters to eliminate scattered excitation light and detected using a photomultiplier tube (PMT). The signal is monitored on a strip chart recorder. DNA sequencing reactions have been carried out utilizing each of the four different dye coupled oligonucleotide primers. In each case a series of peaks are observed on the chart paper. The peaks correspond to fragments of dye labeled DNA of varying lengths synthesized in the sequencing reactions and separated in the gel tube by electrophoresis. Each peak contains of the order of $10^{-14}$ to $10^{-16}$ moles of dye, which is approximately equal to the amount of DNA obtained per band in an equivalent sequencing gel utilizing radioisotope detection. This proves that the fluorescent tag is not removed or degraded from the oligonucleotide primer in the sequencing reactions. It also demonstrates that the detection sensitivity is quite adequate to perform DNA sequence analysis by this means, and that adequate resolution of the DNA fragments is obtained in a tube gel system.

Having fully described the invention it is intended that it be limited only by the lawful scope of the appended claims.

We claim:

1. A novel system for the electrophoretic analysis of oligonucleoide fragments produced in sequencing operations comprising:

a source of chromophore of fluorescent tagged oligonucleotide fragments, said chromophore or fluorophore being distinguishable by its spectral characteristics, a zone for containing an electrophoresis medium, means for introducing said tagged oligonucleotide fragments to said zone; and photometric means for monitoring and distinguishing said tagged DNA fragments upon separation in said medium.

2. The novel system of claim 1 wherein the photometric means is an absorption photometer.

3. The novel system of claim 1 wherein the photometric means is a fluorescent photometer.

4. The novel system of claim 1 wherein the oligonucleotide fragments are labeled with an amino group which is coupled to a dye molecule.

5. The novel system of claim 1 wherein a set of four chromophores or fluorophores are present to tag said oligonucleotide.

6. The novel system of claim 1 wherein said source of tagged oligonucleotide fragments is positioned at one end of said zone, and said detector is positioned in proximity to the opposite end of said zone.

7. A novel system for the electrophoretic analysis of DNA fragments produced in DNA sequencing operations by the chain termination method, comprising:

a source of chromophore or fluorescent tagged DNA fragments from sequencing operations wherein the primer oligonucleotide from each of the four sequencing reactions A, C, G, and T has a different chromophore or fluorescent tag attached to it, each tag being distinguishable from the others by its spectral characteristics.

a zone containing an electrophoresis medium;

means for introducing said tagged DNA fragments to said zone; and photometric means for monitoring and distinguishing said tagged DNA fragments upon separation in said medium.

* * * * *

UNITED STATES PATENT AND TRADEMARK OFFICE
CERTIFICATE OF CORRECTION

PATENT NO. : 5,171,534

DATED : December 15, 1992

INVENTOR(S) : Lloyd M. Smith, et al

It is certified that error appears in the above-indentified patent and that said Letters Patent is hereby corrected as shown below:

Column 10, line 62, delete "of" (second occurrence) and insert therefore --or--.

Signed and Sealed this

Third Day of January, 1995

Attest:

BRUCE LEHMAN

*Attesting Officer*     Commissioner of Patents and Trademarks